US008895270B2

(12) United States Patent
Hidesaki

(10) Patent No.: US 8,895,270 B2
(45) Date of Patent: Nov. 25, 2014

(54) METHOD FOR PRODUCING β-PHENYLALANINE

(75) Inventor: Tomonori Hidesaki, Mobara (JP)

(73) Assignee: Mitsui Chemicals, Inc., Manto-Ku, Tokyo (JP)

( * ) Notice: Subject to any disclaimer, the term of this patent is extended or adjusted under 35 U.S.C. 154(b) by 219 days.

(21) Appl. No.: 12/681,139

(22) PCT Filed: Sep. 30, 2008

(86) PCT No.: PCT/JP2008/002724
§ 371 (c)(1),
(2), (4) Date: Apr. 1, 2010

(87) PCT Pub. No.: WO2009/044531
PCT Pub. Date: Apr. 9, 2009

(65) Prior Publication Data
US 2010/0221793 A1    Sep. 2, 2010

(30) Foreign Application Priority Data

Oct. 1, 2007 (JP) ................................. 2007-257425

(51) Int. Cl.
*C12P 13/22*    (2006.01)
(52) U.S. Cl.
CPC .............. *C12P 13/222* (2013.01); *C12P 13/225* (2013.01)
USPC ....................................................... 435/108
(58) Field of Classification Search
CPC ........ C12N 9/90; C12Y 504/03; C12P 13/22; C12P 13/222
USPC ................................. 435/108, 233
See application file for complete search history.

(56) References Cited

U.S. PATENT DOCUMENTS

| | | | | |
|---|---|---|---|---|
| 3,660,235 | A | * | 5/1972 | Okumura et al. ............. 435/108 |
| 5,518,904 | A | * | 5/1996 | Igarashi et al. ................ 435/108 |
| 5,547,858 | A | * | 8/1996 | Nagano et al. .................... 435/89 |
| 7,452,701 | B2 | * | 11/2008 | Frey et al. ...................... 435/115 |
| 2001/0053847 | A1 | * | 12/2001 | Tang ............................ 536/23.2 |
| 2003/0190713 | A1 | * | 10/2003 | Ueda et al. .................... 435/110 |

FOREIGN PATENT DOCUMENTS

| | | |
|---|---|---|
| JP | 62-000288 A | 1/1987 |
| JP | 9-140391 | 6/1997 |
| WO | WO 2004/021981 | 3/2004 |
| WO | WO 2008/129873 A1 * | 10/2008 |

OTHER PUBLICATIONS

Azuma et al., Appl. Microbiol. Biotechnol. 39:471-476, 1993.*
Anastassiadis, Recent Patents Biotechnol. 1:11-24, 2007.*
Steele et al., Archives Biochem. Biophys. 438:1-10, 2005.*
Stark et al., Advances Biochem. Engineer. Biotechnol. 80:149-175, 2003.*
Magarvey et al., ACS Chemical Biology 3:542-554, Jul. 2008.*
Patnaik et al., Biotechnol. Bioengineer. 99:741-752, Dec. 2007.*
International Search Repot of PCT/JP2008/002724 dated Nov. 18, 2008.
Washington Mutatu et al., "Unusual Mechanism for an Aminomutase Rearrangement: Retention of Configuration at the Migration Termini", Biochemistry, Aug. 28, 2007, vol. 46, No. 34, pp. 9785-9794.
Steven D. Christenson et al., "Kinetic Analysis of the 4-Methylideneimidazole-5-One-Containing Tyrosine Aminomutase in Enediyne Antitumor Antibiotic C-1027 Biosynthesis", Biochemistry, Nov. 4, 2003, vol. 42, No. 43, pp. 12708-12718.
Pascal D. Fortin et al., "A Transglutaminase Homologue as a Condensation Catalyst in Antibiotic Assembly Lines", Nature, Aug. 16, 2007, vol. 448, No. 7155, pp. 824-827.
Karin L. Klettke et al., "β-Styryl-and β-Aryl-β-Alanine Products of Phenylalanine Aminomutase Catalysts", JACS Communications, J. Am. Chem. Soc., vol. 129, No. 22, 2007, pp. 6988-6989.
Japanese Office Action mailed on Jul. 17, 2012, in related Japanese Application No. 2009-535964.
Ronald J. Parry et al., *Biosynthesis of amino Acids. Investigation of the Mechanism of β-Tyrosine Formation*, 102(2) Journal of the American Chemical Society 836-837 (Jan. 16, 1980).
Supplementary European Search Report mailed on Aug. 16, 2013, in corresponding EP Patent Application No. 08835248.9-1501 / 2216410.
Chirpich et al., *Lysine 2,3-Aminomutase—Purification and Properties of a Pyridoxal Phosphate and S-Adenosylmethionine-Activated Enzyme* 245(7) The Journal of Biological Chemistry 1778-1789 (1970).
Kurylo-Borowska et al., *Biosynthesis of β-tyrosine*, 264(1) Biochim. Biophys. Acta. 1-10 (1972).
Wu et al., *Aminomutases: mechanistic diversity, biotechnological applications and future perspectives*, 29(7) Trends in Biotechnology 352-262 (Jul. 2011).

* cited by examiner

*Primary Examiner* — David J Steadman
(74) *Attorney, Agent, or Firm* — Buchanan, Ingersoll & Rooney PC

(57) ABSTRACT

Disclosed is a method for producing a β-amino acid comprising a step of synthesizing a β-amino acid from an α-amino acid in the presence of an amino acid aminomutase. In this method, a β-amino acid is precipitated as a solid in the reaction solution.

6 Claims, No Drawings

SEQUENCE LISTING

```
<160> NUMBER OF SEQ ID NOS: 1

<210> SEQ ID NO 1
<211> LENGTH: 1655
<212> TYPE: DNA
<213> ORGANISM: Artificial
<220> FEATURE:
<223> OTHER INFORMATION: Nucleotide sequence of synthetic gene
<220> FEATURE:
<221> NAME/KEY: CDS
<222> LOCATION: (24)..(1649)

<400> SEQUENCE: 1
gaattcacaa aaaggataaa aca atg tct att gtt aac gaa tcc ggt tct cag      53
                         Met Ser Ile Val Asn Glu Ser Gly Ser Gln
                         1               5                   10 cct gtt gta agc cgt gat gaa acc ctg tcc cag atc gaa cgt acg tcc     101
Pro Val Val Ser Arg Asp Glu Thr Leu Ser Gln Ile Glu Arg Thr Ser
                15                  20                  25 ttc cat atc tct agc ggt aaa gat atc tct ctg gaa gaa atc gca cgt     149
Phe His Ile Ser Ser Gly Lys Asp Ile Ser Leu Glu Glu Ile Ala Arg
        30                  35                  40 gcg gca cgt gac cat cag ccg gta acc ctg cac gac gaa gtt gtg aac     197
Ala Ala Arg Asp His Gln Pro Val Thr Leu His Asp Glu Val Val Asn
    45                  50                  55 cgt gtt acc cgt agc cgt tct att ctg gag tct atg gta tct gac gaa     245
Arg Val Thr Arg Ser Arg Ser Ile Leu Glu Ser Met Val Ser Asp Glu
60                  65                  70 cgt gtt atc tat ggt gtc aac acc agc atg ggc ggt ttt gtt aac tac     293
Arg Val Ile Tyr Gly Val Asn Thr Ser Met Gly Gly Phe Val Asn Tyr
75                  80                  85                  90
```

```
atc gtt ccg atc gct aag gca agc gaa ctg cag aac aac ctg att aat    341
Ile Val Pro Ile Ala Lys Ala Ser Glu Leu Gln Asn Asn Leu Ile Asn
             95                 100                 105 gcc gtt gct acc aac gtc ggc aaa tac ttc gat gat acc acc gtc cgc    389
Ala Val Ala Thr Asn Val Gly Lys Tyr Phe Asp Asp Thr Thr Val Arg
        110                 115                 120 gca acc atg ctg gca cgt atc gtc tct ctg tct cgc ggt aac tct gcg    437
Ala Thr Met Leu Ala Arg Ile Val Ser Leu Ser Arg Gly Asn Ser Ala
        125                 130                 135 att tct atc gtc aat ttc aaa aag ctg atc gaa att tac aac cag ggt    485
Ile Ser Ile Val Asn Phe Lys Lys Leu Ile Glu Ile Tyr Asn Gln Gly
140                 145                 150 atc gtt ccg tgt atc ccg gaa aaa ggc tcc ctg ggt act tcc ggt gat    533
Ile Val Pro Cys Ile Pro Glu Lys Gly Ser Leu Gly Thr Ser Gly Asp
155                 160                 165                 170 ctg ggt ccg ctg gcc gcg atc gcc ctg gta tgc acc ggc cag tgg aaa    581
Leu Gly Pro Leu Ala Ala Ile Ala Leu Val Cys Thr Gly Gln Trp Lys
                175                 180                 185 gct cgt tac cag ggt gaa cag atg agc ggc gca atg gct ctg gag aaa    629
Ala Arg Tyr Gln Gly Glu Gln Met Ser Gly Ala Met Ala Leu Glu Lys
        190                 195                 200 gcg ggc att tcc ccg atg gag ctg tcc ttc aaa gaa ggt ctg gcg ctg    677
Ala Gly Ile Ser Pro Met Glu Leu Ser Phe Lys Glu Gly Leu Ala Leu
        205                 210                 215 atc aac ggt acc tct gct atg gtt ggt ctg ggt gta ctg ctg tat gac    725
Ile Asn Gly Thr Ser Ala Met Val Gly Leu Gly Val Leu Leu Tyr Asp
220                 225                 230 gag gtg aag cgt ctg ttc gat acc tac ctg act gta act tct ctg tct    773
Glu Val Lys Arg Leu Phe Asp Thr Tyr Leu Thr Val Thr Ser Leu Ser
235                 240                 245                 250 atc gag ggt ctg cat ggt aaa act aaa ccg ttt gag cct gcg gta cac    821
Ile Glu Gly Leu His Gly Lys Thr Lys Pro Phe Glu Pro Ala Val His
                255                 260                 265 cgt atg aaa ccg cac cag ggc cag ctg gaa gta gct acc acc atc tgg    869
Arg Met Lys Pro His Gln Gly Gln Leu Glu Val Ala Thr Thr Ile Trp
        270                 275                 280 gaa acc ctg gca gat tcc tcc ctg gcc gtt aac gaa cac gaa gtg gaa    917
Glu Thr Leu Ala Asp Ser Ser Leu Ala Val Asn Glu His Glu Val Glu
        285                 290                 295 aag ctg atc gct gaa gaa atg gac ggc ctg gta aaa gct agc aac cac    965
Lys Leu Ile Ala Glu Glu Met Asp Gly Leu Val Lys Ala Ser Asn His
300                 305                 310 cag atc gaa gac gcc tac tct atc cgt tgt act ccg caa atc ctg ggc   1013
Gln Ile Glu Asp Ala Tyr Ser Ile Arg Cys Thr Pro Gln Ile Leu Gly
315                 320                 325                 330 ccg gta gca gac acc ctg aaa aac att aaa cag acc ctg acc aac gaa   1061
Pro Val Ala Asp Thr Leu Lys Asn Ile Lys Gln Thr Leu Thr Asn Glu
                335                 340                 345 ctg aac tct tct aac gat aac ccg ctg att gat cag acc acc gaa gaa   1109
Leu Asn Ser Ser Asn Asp Asn Pro Leu Ile Asp Gln Thr Thr Glu Glu
        350                 355                 360 gta ttc cac aac ggc cac ttc cac ggt cag tat gta tct atg gcg atg   1157
Val Phe His Asn Gly His Phe His Gly Gln Tyr Val Ser Met Ala Met
        365                 370                 375 gat cac ctg aac att gct ctg gtt acc atg atg aat ctg gcc aac cgt   1205
Asp His Leu Asn Ile Ala Leu Val Thr Met Met Asn Leu Ala Asn Arg
380                 385                 390 cgc atc gac cgt ttc atg gat aaa tct aac tcc aac ggt ctg ccg ccg   1253
Arg Ile Asp Arg Phe Met Asp Lys Ser Asn Ser Asn Gly Leu Pro Pro
395                 400                 405                 410
```

```
ttc ctg tgc gca gaa aac gct ggt ctg cgt ctg ggt ctg atg ggc ggt      1301
Phe Leu Cys Ala Glu Asn Ala Gly Leu Arg Leu Gly Leu Met Gly Gly
            415                     420                 425 cag ttc atg act gcg agc atc acc gct gaa tcc cgc gca tcc tgt atg      1349
Gln Phe Met Thr Ala Ser Ile Thr Ala Glu Ser Arg Ala Ser Cys Met
            430                     435                 440 ccg atg tct att cag tcc ctg agc act act ggt gat ttc cag gac atc      1397
Pro Met Ser Ile Gln Ser Leu Ser Thr Thr Gly Asp Phe Gln Asp Ile
            445                     450                 455 gtt agc ttc ggc ctg gtt gct gcc cgc cgt gta cgt gaa cag ctg aaa      1445
Val Ser Phe Gly Leu Val Ala Ala Arg Arg Val Arg Glu Gln Leu Lys
            460                     465                 470 aac ctg aag tat gtg ttt tct ttc gaa ctg ctg tgt gcg tgc cag gca      1493
Asn Leu Lys Tyr Val Phe Ser Phe Glu Leu Leu Cys Ala Cys Gln Ala
475                     480                     485                 490 gtt gac atc cgt ggt act gcg ggt ctg tct aaa cgt acc cgt gcc ctg      1541
Val Asp Ile Arg Gly Thr Ala Gly Leu Ser Lys Arg Thr Arg Ala Leu
                495                     500                 505 tac gat aaa acc cgt acc ctg gta ccg tat ctg gaa gaa gat aaa acc      1589
Tyr Asp Lys Thr Arg Thr Leu Val Pro Tyr Leu Glu Glu Asp Lys Thr
            510                     515                 520 att tct gat tat atc gaa tct att gcg caa acc gtg ctg acc aaa aac      1637
Ile Ser Asp Tyr Ile Glu Ser Ile Ala Gln Thr Val Leu Thr Lys Asn
            525                     530                 535 tct gac atc tga aagctt                                                1655
Ser Asp Ile
            540
```

METHOD FOR PRODUCING β-PHENYLALANINE

TECHNICAL FIELD

The present invention relates to a method for producing a β-amino acid comprising a step of synthesizing a β-amino acid from an α-amino acid in the presence of an amino acid aminomutase.

BACKGROUND ART

A β-amino acid has been known as a compound that is useful as an intermediate for medicaments. In the past, in order to obtain a β-amino acid stereoselectively, there has been used a method for isolating and purifying a desired stereoisomer by optically resolving a racemic β-amino acid. However, according to this method, a theoretical yield is as low as 50% and this method becomes complicated due to multiple steps involved. So, the resulting β-amino acid becomes expensive as well. Accordingly, a method for producing a β-amino acid capable of realizing high efficiency and reducing the cost is expected to be developed.

In late years, it has been reported that there exists an amino acid aminomutase capable of catalyzing the reaction for synthesizing a β-amino acid using an L-amino acid which is relatively inexpensively available as a substrate.

For example, in Non-patent Document 1, there has been reported a method for synthesizing (R)-β-phenylalanine from L-phenylalanine using a phenylalanine aminomutase derived from *Taxus caspidata*.

Meanwhile, in Non-patent Document 2, there has been reported a method for synthesizing β-tyrosine from L-tyrosine using a tyrosine aminomutase derived from *Streptomyces globisporus*.

In addition, in Non-patent Document 3, it has been reported that β-phenylalanine is synthesized from L-phenylalanine using AdmH derived from *Pantoea agglomerans* strain Eh335.

Non-patent Document 1: Biochemistry, 46 (2007), pp. 9785-9794
Non-patent Document 2: Biochemistry, 42 (2003), pp. 12708-12718
Non-patent Document 3: Nature, 448 (2007), pp. 824-827
Non-patent Document 4: J. Am. Chem. Soc., 129 (2007), pp. 6988-6989

DISCLOSURE OF THE INVENTION

However, in all cases of the above prior arts, β-amino acids are synthesized for the purpose of characterization of enzymes, the reaction yield and quantity are low, and complicated operations are further expected to be needed for isolation and purification. So, such methods are not considered industrially advantageous. The β-amino acid is a compound useful as a medicinal material or the like, and a production method for carrying out the enzyme reaction itself with high efficiency is expected to be developed.

An object of the present invention is to produce a β-amino acid with high efficiency in a method for producing a β-amino acid through the enzyme reaction.

According to the present invention, there is provided a method for producing a β-amino acid comprising a step of synthesizing a β-amino acid from an α-amino acid in the presence of an amino acid aminomutase, in which a β-amino acid is precipitated as a solid in the reaction solution.

According to this invention, a β-amino acid is precipitated as a solid, whereby it is possible to efficiently carry out an enzyme reaction with an amino acid aminomutase, while a solid is further collected from a reaction solution, whereby it is possible to easily purify the product.

According to the present invention, a method for producing a β-amino acid with high efficiency is provided.

BEST MODE FOR CARRYING OUT THE INVENTION

An embodiment according to the present invention relates to a method for producing an aromatic β-amino acid. This production method involves a step of synthesizing an aromatic β-amino acid from an aromatic α-amino acid in the presence of an aromatic amino acid aminomutase, in which an aromatic β-amino acid is precipitated as a solid in a reaction solution.

Examples of the aromatic amino acid aminomutase include a phenylalanine aminomutase and a tyrosine aminomutase. Examples of the phenylalanine aminomutase include an (S)-selective phenylalanine aminomutase and an (R)-selective phenylalanine aminomutase.

In this specification, "(S)-selective phenylalanine aminomutase" refers to a protein having an (S)-selective phenylalanine aminomutase activity. Furthermore, "(S)-selective phenylalanine aminomutase activity" means that β-phenylalanine can be synthesized in an (S)-form-selective manner. "(S)-form-selective manner" means that the optical purity of (S)-β-phenylalanine contained in β-phenylalanine is not less than 50% ee, preferably not less than 80% ee, further preferably not less than 90% ee and most preferably not less than 99% ee.

Meanwhile, in this specification, "(R)-selective phenylalanine aminomutase" refers to a protein having an (R)-selective phenylalanine aminomutase activity. Furthermore, "(R)-selective phenylalanine aminomutase activity" means that β-phenylalanine can be synthesized in an (R)-form-selective manner. "(R)-form-selective manner" means that the optical purity of (R)-β-phenylalanine contained in β-phenylalanine is not less than 50% ee, preferably not less than 80% ee, further preferably not less than 90% ee and most preferably not less than 99% ee.

Examples of the aromatic α-amino acid include L-phenylalanine, L-tyrosine and analogues thereof.

Examples of the aromatic β-amino acid include β-phenylalanine, β-tyrosine and analogues thereof. Examples of β-phenylalanine include (S)-β-phenylalanine and (R)-β-phenylalanine. Furthermore, examples of β-tyrosine include (S)-β-tyrosine and (R)-β-tyrosine.

The (R)-selective phenylalanine aminomutase catalyzes the reaction for synthesizing (R)-β-phenylalanine from L-phenylalanine. Furthermore, it is also capable of catalyzing the reaction for synthesizing corresponding (R)-β-phenylalanine analogues from L-phenylalanine analogues (refer to Non-patent Document 4). Examples of L-phenylalanine analogues include L-4-fluorophenylalanine, 3-(2-thienyl)-L-alanine, L-4-methoxyphenylalanine, L-2-fluorophenylalanine, L-4-methylphenylalanine and the like. Examples of (R)-β-phenylalanine analogues include (R)-β-4-fluorophenylalanine, (R)-β-3-(2-thienyl)-alanine, (R)-β-4-methoxyphenylalanine, (R)-β-2-fluorophenylalanine, (R)-β-4-methylphenylalanine and the like.

The tyrosine aminomutase catalyzes the reaction for synthesizing β-tyrosine from L-tyrosine. Furthermore, L-tyrosine analogues may also be used as substrates (Non-patent Document 2). Examples of L-tyrosine analogues include L-3,4-dihydroxyphenylalanine, L-3-chlorotyrosine and the like.

It has been known that the reaction catalyzed by the aromatic amino acid aminomutase is reversible in the synthesis of an aromatic β-amino acid from an aromatic α-amino acid and its yield is low. The reaction catalyzed by the aromatic amino acid aminomutase depends on the reaction conditions such as pH, temperature and the like. However, when the reaction reaches a state of equilibrium, the concentrations of the substrate and the product become approximately the same level and its maximum reaction yield remains approximately 60%. For example, in Non-patent Document 1, it has been reported that the yield of the (R)-β-phenylalanine synthesis reaction using a phenylalanine aminomutase is 53±1%. Furthermore, in Non-patent Document 2, it has been reported that the maximum yield of the β-tyrosine synthesis reaction using a tyrosine aminomutase is ~60%. In Non-patent Document 3, an equilibrium constant of the β-phenylalanine synthesis reaction using AdmH is 1.28, while the yield from the equilibrium constant is determined as about 56%.

In this Embodiment, "precipitated as a solid" means that the aromatic β-amino acid is synthesized beyond the saturation concentration or supersaturation concentration in the reaction solution and the excess comes out of solution as a solid. In the reaction catalyzed by the aromatic amino acid aminomutase, when the reaction proceeds while precipitating the aromatic β-amino acid as a solid, the aromatic β-amino acid can be produced with high efficiency. When the reaction proceeds while precipitating the solid of the product in the β-phenylalanine synthesis reaction with a phenylalanine aminomutase and the reaction reaches a state of equilibrium, the solid of the product is precipitated in the reaction solution, while, the concentrations of the substrate and the product that are dissolved become approximately the same level. At this time, the greater the amount of the generated product precipitated is, the higher the reaction yield and quantity are. Furthermore, by collecting the solid from the reaction solution, the product is easily purified.

In the aromatic amino acid aminomutase reaction, it is possible to proceed with the reaction while precipitating the aromatic β-amino acid as a solid by optimizing the relationship between the synthesized amount and the solubility of the aromatic β-amino acid. The amount of the aromatic β-amino acid synthesized depends naturally on properties of an enzyme in use, and it also varies depending on the reaction conditions such as pH, temperature and the amount of the substrate added. Furthermore, the solubility of the aromatic β-amino acid varies depending on pH and temperature of the reaction solution. Accordingly, it is possible to proceed with the reaction while precipitating the aromatic β-amino acid as a solid by optimizing pH and temperature of the reaction solution, and the amount of the substrate added.

In order to increase the amount of the aromatic β-amino acid precipitated, and to improve the reaction yield and quantity, for example, the reaction may be carried out under the condition of low solubility of the aromatic β-amino acid.

Meanwhile, in order to increase the amount of the aromatic β-amino acid precipitated, and to improve the reaction yield and quantity, the reaction may be carried out by increasing the amount of the substrate added. Concretely, the amount of the aromatic α-amino acid added into the reaction system can be not less than 2.5 weight % (wt %), more preferably not less than 7 weight % (wt %) and further preferably not less than 16 weight % (wt %). There is no particular upper limit of the amount of the aromatic α-amino acid added into the reaction system. When the added amount is excessively high, the solid volume in the reaction system becomes high so that the stirring efficiency is lowered. So, the formation rate of the aromatic β-amino acid is reduced. Accordingly, it is preferably not more than 60 weight % (wt %), more preferably not more than 50 weight % (wt %) and further preferably not more than 40 weight % (wt %). The aromatic α-amino acid is added in an amount such that the reaction solution can be properly stirred, whereby the reaction can be carried out with high efficiency.

In accordance with a method for adding a substrate, the substrate may be added at once upon the initiation of reaction, at several different times, or continuously along with the progress of reaction. Further, the substrate may be present as a solid in the reaction solution.

For example, when the phenylalanine aminomutase is used, pH of the reaction solution may be set from 6 to 10. When pH is set to less than 6, an enzyme activity of the phenylalanine aminomutase is lowered. So, the formation rate of β-phenylalanine becomes slower. Moreover, when pH is set to greater than 10, the solubility of β-phenylalanine becomes excessively high. Accordingly, the amount of β-phenylalanine precipitated as a solid is reduced so that the reaction yield and quantity cannot be improved.

Meanwhile, the temperature of the reaction solution is not less than 4 degrees centigrade, and may be not more than a temperature in which an aromatic amino acid aminomutase is deactivated. When the temperature of the reaction solution is less than 4 degrees centigrade, an enzyme activity of the aromatic amino acid aminomutase is lowered. So, the formation rate of the aromatic β-amino acid becomes slower.

The temperature of deactivation refers to a temperature in which 50% or more of the aromatic amino acid aminomutase is deactivated for 10 minutes in the reaction solution. When the temperature is set to higher than the temperature of deactivation, the amount of the aromatic amino acid aminomutase to function in an effective manner is reduced so that the formation rate of the aromatic β-amino acid becomes slower.

When the phenylalanine aminomutase is used, the reaction temperature can be set to not less than 4 degrees centigrade. Thus, an enzyme activity of the phenylalanine aminomutase becomes high so that the formation rate of β-phenylalanine can be improved. The reaction temperature is more preferably set to not less than 15 degrees centigrade. Therefore, the reaction can be carried out with much higher efficiency.

Meanwhile, when the phenylalanine aminomutase is used, the temperature of the reaction solution may be set to not more than 60 degrees centigrade. Thus, an enzyme activity of the phenylalanine aminomutase can be maintained stably and the reaction can be carried out with high efficiency.

In order to increase the amount of the aromatic β-amino acid precipitated in the reaction with the aromatic amino acid aminomutase and further to complete the reaction further within a short period of time, the reaction can be carried out under the condition of high enzyme activity at the early stage and under the condition of low solubility of the generated product at the final stage. An example thereof includes a method of varying the temperature of the reaction solution at the early stage and final stage of the reaction. Concretely, the lower limit may be set to 20 degrees centigrade and the upper limit may be set to a temperature in which the aromatic amino acid aminomutase is deactivated at the early stage of the reaction. Moreover, the temperature may be from 4 to 30 degrees centigrade at the final stage of the reaction.

Incidentally, for the (S)-selective phenylalanine aminomutase and (R)-selective phenylalanine aminomutase, optimum pHs and optimum temperatures are similar. For (S)-β-phenylalanine and (R)-β-phenylalanine, the solubilities are similar. Accordingly, a method for producing (S)-β-phenylalanine using an (S)-selective phenylalanine aminomutase is examined and as a result, it can be applied also to a method for producing (R)-β-phenylalanine from the fact that properties of both enzymes and physical properties of the products are similar.

The aromatic amino acid aminomutase can be obtained from an aromatic amino acid aminomutase-producing organism. Examples of the aromatic amino acid aminomutase-producing organism include a plant belonging to the genus *Taxus*, a bacterium belonging to the genus *Pantoea*, a bacterium belonging to the genus *Bacillus*, a bacterium belonging to the genus *Streptomyces*, and a bacterium belonging to the genus *Chondromyces*. The examples include *Taxus brevifolia, Taxus caspidata, Taxus chinensis, Taxus*×media cv *Hicksii, Pantoea agglomerans* strain Eh335, *Bacillus brevis* Vm4, *Streptomyces globisporus*, and *Chondromyces crocatus* Cm c5. *Taxus brevifolia, Taxus chinensis* and *Taxus*×media cv *Hicksii* are phenylalanine aminomutase-producing organisms. *Taxus caspidata* is an (R)-selective phenylalanine aminomutase-producing organism. *Pantoea agglomerans* strain Eh335 is an (S)-selective phenylalanine aminomutase-producing organism. Moreover, *Bacillus brevis* Vm4, *Streptomyces globisporus* and *Chondromyces crocatus* Cm c5 are tyrosine aminomutase-producing organisms.

Meanwhile, a host cell may be transformed with a DNA encoding an aromatic amino acid aminomutase, and the aromatic amino acid aminomutase is expressed and isolated. According to this method, the aromatic amino acid aminomutase can be obtained in a simple and effective manner.

The aromatic amino acid aminomutase to be used in the reaction may be a purified one, an aromatic amino acid aminomutase-producing organism, a transformant transformed with a DNA encoding an aromatic amino acid aminomutase or a treated product thereof.

The treated product can be obtained by allowing the cell to be subjected to mechanical disruption, ultrasonication, freezing and thawing treatment, drying treatment, pressurization or depressurization treatment, osmotic pressure treatment, autodigestion, surfactant treatment, or enzyme treatment for the purpose of cell disruption. Also, the treated product can be obtained as an immobilized fraction or an immobilized cell, which contains an aromatic amino acid aminomutase obtained by such treatments.

The amount of the aromatic amino acid aminomutase in use is not particularly limited as long as the reaction with the aromatic α-amino acid fully proceeds. As for the method of adding an aromatic amino acid aminomutase, the aromatic amino acid aminomutase may be added at once at the initial stage of the reaction, at several different times, or continuously.

As a medium used for a reaction solution, there is used water, an aqueous medium, an organic solvent, or a mixture solution of water or an aqueous medium and an organic solvent. As the aqueous medium, there is used, for example, a buffer solution such as a phosphate buffer solution, a HEPES (N-2-hydroxyethylpiperazine-N-ethanesulfonic acid) buffer solution, a Tris[Tris(hydroxymethyl)aminomethane]hydrochloric acid buffer solution or the like. Any organic solvent may be used as long as it does not hinder the reaction.

The reaction time is not particularly limited as long as a solid of an aromatic β-amino acid can be precipitated. Accordingly, it is preferred to secure the reaction time required, at least, for the amount of the β-amino acid synthesized in the reaction solution to exceed the solubility of the aromatic β-amino acid. The reaction time may be properly determined depending on the amount of the aromatic β-amino acid aminomutase.

The aromatic β-amino acid can be isolated and purified from the reaction solution in accordance with a method that is used in general organic synthetic chemistry, such as extraction using an organic solvent, crystallization, thin-layer chromatography, high performance liquid chromatography or the like. According to the crystallization process, the aromatic β-amino acid can be purified by filtering the reaction solution and recrystallizing the resulting solid. Furthermore, the solid precipitated in the reaction solution is once dissolved to remove a bacterial cell components, and then to precipitate a crystal, whereby the aromatic β-amino acid can be purified as well.

Examples of the present invention will hereafter be described. However, the present invention is not restricted to these Examples.

EXAMPLES

Analysis Conditions (S)-β-phenylalanine, (R)-β-phenylalanine and L-phenylalanine were quantitatively analyzed by the high performance liquid chromatography. These analysis conditions are as follows.

(1) Conditions for Analyzing (S)-β-phenylalanine and (R)-β-phenylalanine

An object of the analysis of (1) was to mainly measure the optical purity of β-phenylalanine.

Column; CHIRALPAK WH 4.6×250 (Daicel Chemical Industries, Ltd.)
Column temperature; 50 degrees centigrade
Pump flow rate; 1.5 ml/min
Eluent; 2 mmol/l copper sulfate
Detection; UV 254 nm In the analysis conditions, the detection limit of any of (S)-β-phenylalanine and (R)-β-phenylalanine was approximately $1\times10^{-4}$ weight % (wt %).

(2) Conditions for Analyzing β-phenylalanine and L-phenylalanine

An object of the analysis of (2) was to mainly measure the reaction yield.

Column; Develosil TMS-UG-5 4.6×250 (Nomura Chemical Co., Ltd.)
Column temperature; 40 degrees centigrade
Pump flow rate; 1.0 ml/min
Eluent; 5 mmol/l citric acid buffer solution (pH 6.0):methanol=8:2 (v/v)
Detection; UV 254 nm Evaluation Method The optical purity of (S)-β-phenylalanine was calculated from the peak area of the chromatogram obtained under analysis conditions illustrated in (1) above. Furthermore, the reaction yield of (S)-β-phenylalanine was calculated from the peak area of the chromatogram obtained under analysis conditions illustrated in (2) above. Concretely, when the reaction solution contained a solid of β-phenylalanine or a solid of L-phenylalanine, a solution obtained by collecting a part of the reaction solution containing these solids, mixing with a 0.2 mol/l hydrochloric acid solution and dissolving these solids was analyzed. The amount (g) of (S)-β-phenylalanine synthesized was calculated from the peak area of the chromatogram using a calibration curve of (S)-β-phenylalanine standards to determine the yield from (Formula 1).

Yield (%)=Amount of (S)-β-phenylalanine synthesized (g)/Amount of L-phenylalanine added (g)×100     (Formula 1)

Example 1

Production of Transformant Expressing (S)-selective Phenylalanine Aminomutase (1) Synthesis of DNA Encoding (S)-selective Phenylalanine Aminomutase A DNA having a nucleotide sequence set forth in SEQ ID NO: 1 was entrusted to DNA2.0 Inc. and synthesized. The synthesized DNA had EcoRI and HindIII restriction enzyme recognition sequences near the 5' and 3' ends, respectively.

(2) Production of Recombinant DNA

A recombinant plasmid was produced as a recombinant DNA. The synthesized DNA and plasmid pUC18 were digested with EcoRI and HindIII, followed by ligation using Ligation High (a product of Toyobo, Co., Ltd.). Thereafter, the obtained recombinant plasmid was used for transformation of *Escherichia coli* DH5α (a product of Toyobo, Co., Ltd.). The transformant was cultured in an LB agar medium containing 100 μg/ml of ampicillin (Am) and X-Gal (5-bromo-4-chloro-3-indolyl-β-D-galactoside). Thus, an Am-resistant transformant that was formed into a white colony was obtained. A plasmid was extracted from the thus-obtained transformant.

The nucleotide sequence of the DNA fragment that had been introduced into the plasmid was confirmed to be the nucleotide sequence set forth in SEQ ID NO: 1 in accordance with a usual method for nucleotide sequencing. The obtained plasmid having a DNA encoding (S)-selective phenylalanine aminomutase was designated as pSPAM.

(3) Production and Expression of Transformant

*Escherichia coli* DH5α was transformed by a usual method using pSPAM, and the obtained transformant was designated as MT-11046. An LB medium (100 ml) containing 100 μg/ml of Am was inoculated with the transformant in a 500-ml baffled Erlenmeyer flask. The resulting material was shake-cultured at 30 degrees centigrade until OD (660 nm) reached 0.5. Then, IPTG (isopropyl-β-thiogalactopyranoside) was added thereto such that the medium contained 1 mmol/l. This was followed by further shake culture for 16 hours. The culture solution was centrifuged at 8,000 rpm for 20 minutes. The obtained bacterial cell was cryopreserved at −20 degrees centigrade as it was or suspended in a 0.1 mol/l Tris hydrochloric acid buffer solution (pH 8.0), followed by cryopreservation at −20 degrees centigrade.

Example 2

Production of (S)-β-phenylalanine with (S)-selective Phenylalanine Aminomutase The reaction solution (4.0 g) containing 8 weight % (wt %) of L-phenylalanine, 0.4 g of a 1 mol/l Tris hydrochloric acid buffer solution (pH 8.5), a bacterial cell suspension (in an appropriate amount) of MT-11046 produced in Example 1 and water was reacted at 25 degrees centigrade for 48 hours. A part of the solid in the reaction solution was collected and analyzed under the analysis conditions as described above, whereby a solid of (S)-β-phenylalanine precipitated was observed. The reaction yield of (S)-β-phenylalanine was 83%. It was confirmed that (R)-β-phenylalanine was not more than the detection limit and the optical purity was not less than 99.5% ee.

Comparative Example 1

Production of (S)-β-phenylalanine with (S)-selective Phenylalanine Aminomutase (Production of (S)-β-phenylalanine Under Reaction Conditions as Described in Non-patent Document 3)

The reaction solution (4.0 g) containing $1.7 \times 10^{-2}$ weight % (wt %) of L-phenylalanine, 0.8 g of a 100 mmol/l tricine buffer solution (pH 8.25), a bacterial cell suspension (in an appropriate amount) of MT-11046 produced in Example 1 and water was reacted at 30 degrees centigrade for 4 hours. Without precipitating a solid of (S)-β-phenylalanine in the reaction solution, the reaction yield of (S)-β-phenylalanine was 48%.

Example 3

Production of (S)-β-phenylalanine [Examination 1 of pH]

The reaction solution (250 g) containing 12 weight % (wt %) of L-phenylalanine, a bacterial cell (in an appropriate amount) of MT-11046 produced in Example 1 and water was reacted at 25 degrees centigrade for 24 hours or more. During the reaction, pH of the reaction solution was adjusted to each pH shown in Table 1 with 25% ammonia water. A solid of (S)-β-phenylalanine precipitated under all examined conditions was observed. The reaction yields of (S)-β-phenylalanine in respective pHs are shown in Table 1.

TABLE 1

| pH | Yield |
|---|---|
| 6.3 | 61% |
| 6.6 | 83% |
| 7.0 | 87% |
| 7.4 | 85% |
| 7.6 | 88% |
| 7.8 | 89% |
| 8.0 | 88% |
| 8.2 | 86% |
| 8.4 | 82% |
| 8.8 | 62% |

Comparative Example 2

Production of (S)-β-phenylalanine

The reaction solution (250 g) containing 12 weight % (wt %) of L-phenylalanine, a bacterial cell (in an appropriate amount) of MT-11046 produced in Example 1 and water was reacted at 25 degrees centigrade for 24 hours or more. During the reaction, pH of the reaction solution was adjusted to each pH shown in Table 2 with a 6 mol/l hydrochloric acid solution or 25% ammonia water. A solid of (S)-β-phenylalanine unprecipitated under all examined conditions was observed. The reaction yields of (S)-β-phenylalanine in respective pHs are shown in Table 2.

TABLE 2

| pH | Yield |
|---|---|
| 5.5 | 10% |
| 10.5 | 5% |

Example 4

Production of (S)-β-phenylalanine [Examination 2 of pH]

The reaction solution (250 g) containing 36 weight % (wt %) of L-phenylalanine, a bacterial cell (in an appropriate amount) of MT-11046 produced in Example 1 and water was reacted at 25 degrees centigrade for 24 hours or more. During the reaction, pH of the reaction solution was adjusted to each pH shown in Table 3 with 25% ammonia water. A solid of (S)-β-phenylalanine precipitated under all examined conditions was observed. The reaction yields of (S)-β-phenylalanine in respective pHs are shown in Table 3.

TABLE 3

| pH | Yield |
| --- | --- |
| 6.5 | 79% |
| 7.5 | 92% |
| 8.0 | 93% |
| 8.8 | 72% |

Example 5

Production of (S)-β-phenylalanine [Examination 3 of pH]

The reaction solution (250 g) containing 12 weight % (wt %) of L-phenylalanine, a bacterial cell (in an appropriate amount) of MT-11046 produced in Example 1 and water was reacted at 20 degrees centigrade for 24 hours or more. During the reaction, pH of the reaction solution was adjusted to 9.2 with 25% ammonia water. A solid of (S)-β-phenylalanine precipitated under examined condition was observed. The reaction yield of (S)-β-phenylalanine was 62%.

Comparative Example 3

Production of (S)-β-phenylalanine

The reaction solution (250 g) containing 36 weight % (wt %) of L-phenylalanine, a bacterial cell (in an appropriate amount) of MT-11046 produced in Example 1 and water was reacted at 25 degrees centigrade for 24 hours or more. During the reaction, pH of the reaction solution was adjusted to each pH shown in Table 4 with a 6 mol/l hydrochloric acid solution or 25% ammonia water. A solid of (S)-β-phenylalanine unprecipitated under all examined conditions was observed. The reaction yields of (S)-β-phenylalanine in respective pHs are shown in Table 4.

TABLE 4

| pH | Yield |
| --- | --- |
| 5.5 | 5% |
| 10.5 | 3% |

Example 6

Production of (S)-β-phenylalanine [Examination 1 of Temperature]

The reaction solution (4.0 g) containing 12 weight % (wt %) of L-phenylalanine, 0.4 g of a 1 mol/l Tris hydrochloric acid buffer solution (pH 8.5), a bacterial cell suspension (in an appropriate amount) of MT-11046 produced in Example 1 and water was reacted at each temperature shown in Table 5 for 24 hours or more. A solid of (S)-β-phenylalanine precipitated under all examined conditions was observed. The reaction yields of (S)-β-phenylalanine in respective temperatures are shown in Table 5.

TABLE 5

| Temperature | Yield |
| --- | --- |
| 4° C. | 93% |
| 15° C. | 90% |
| 25° C. | 88% |
| 30° C. | 86% |
| 40° C. | 74% |
| 50° C. | 63% |
| 60° C. | 44% |

Example 7

Production of (S)-β-phenylalanine [Examination 2 of Temperature]

The reaction solution (250 g) containing 36 weight % (wt %) of L-phenylalanine, a bacterial cell (in an appropriate amount) of MT-11046 produced in Example 1 and water was reacted at each temperature shown in Table 6 for 24 hours or more. During the reaction, pH of the reaction solution was adjusted to 8.0 with 25% ammonia water. A solid of (S)-β-phenylalanine precipitated under all examined conditions was observed. The reaction yields of (S)-β-phenylalanine in respective temperatures are shown in Table 6.

TABLE 6

| Temperature | Yield |
| --- | --- |
| 15° C. | 94% |
| 25° C. | 93% |
| 35° C. | 89% |

Example 8

Production of (S)-3-phenylalanine [Examination 1 of Amount of Substrate Added]

The reaction solution (4.0 g) containing each amount shown in Table 7 of L-phenylalanine to be added, 0.4 g of a 1 mol/l Tris hydrochloric acid buffer solution (pH 8.5), a bacterial cell suspension (in an appropriate amount) of MT-11046 produced in Example 1 and water was reacted at 25 degrees centigrade for 24 hours or more. A solid of (S)-β-phenylalanine precipitated under all examined conditions was observed. The reaction yields of (S)-β-phenylalanine with respective amounts of substrate added are shown in Table 7.

TABLE 7

| Amount of Substrate Added Weight % (wt %) | Yield |
| --- | --- |
| 7% | 81% |
| 16% | 90% |
| 24% | 93% |
| 36% | 94% |

Example 9

Production of (S)-β-phenylalanine [Examination 2 of Amount of Substrate Added]

The reaction solution (4.0 g) containing each amount shown in Table 8 of L-phenylalanine to be added, 0.4 g of a 1 mol/l Tris hydrochloride buffer solution (pH 8.5), a bacterial cell suspension (in an appropriate amount) of MT-11046 produced in Example 1 and water was reacted at 10 degrees centigrade for 24 hours or more. A solid of (S)-β-phenylalanine precipitated under all examined conditions was observed. The reaction yields of (S)-β-phenylalanine with respective amounts of substrate added are shown in Table 8.

TABLE 8

| Amount of Substrate Added Weight % (wt %) | Yield |
|---|---|
| 2.5% | 62% |
| 3.0% | 65% |

Example 10

Purification of (S)-β-phenylalanine

In Example 3, 6 mol/l hydrochloric acid was added to the reaction solution prepared at pH 8.0 to adjust pH to 2.1 so that (S)-β-phenylalanine precipitated as a solid was dissolved. Thereafter, 16 g of activated carbon (50% water content) was added thereto and the resulting solution was stirred at 25 degrees centigrade for 30 minutes before filtering the solution to remove the activated carbon and the bacterial cell components. Next, the activated carbon was washed with 32 g of water and the solution was combined with the filtrate. Then, the mixture solution was adjusted its pH to 5.6 with a 20% sodium hydroxide aqueous solution while being stirred calmly at 10 degrees centigrade and (S)-β-phenylalanine was precipitated. The crystallization liquid was filtered and the crystal was washed with 30 ml of cold water three times. After drying, 21.6 g of (S)-β-phenylalanine of a white crystal was obtained. An aqueous solution of the crystal was analyzed by HPLC and as a result, it was confirmed that (R)-β-phenylalaninewas not more than the detection limit and the optical purity was not less than 99.5% ee.

As described above, Embodiments and Examples of the present invention were illustrated. However, Embodiments and Examples are exemplified in the present invention and various configurations other than those illustrated above may also be adopted. For example, in Embodiments, a method for producing an aromatic β-amino acid with an aromatic amino acid aminomutase was exemplified, whereas the present invention can also be applied to amino acids other than the aromatic amino acid. For example, by using lysine 2,3-aminomutase, it is possible to produce β-lysine. Furthermore, by using arginine 2,3-aminomutase, it is also possible to produce β-arginine. By using glutamate 2,3-aminomutase, it is also possible to produce β-glutamic acid. By using leucine 2,3-aminomutase, it is also possible to produce β-leucine.

The invention claimed is:

1. A method for producing (S)-β-phenylalanine from L-phenylalanine comprising:
   providing a reaction solution comprising an (S)-selective phenylalanine aminomutase, wherein said (S)-selective phenylalanine aminomutase synthesizes (S)-β-phenylalanine from L-phenylalanine;
   synthesizing (S)-β-phenylalanine beyond a saturation concentration or supersaturation concentration in said reaction solution, wherein said (S)-β-phenylalanine is precipitated out of the reaction solution as a solid; and
   collecting said solid (S)-β-phenylalanine from said reaction solution.

2. A method for producing (R)-β-phenylalanine from L-phenylalanine comprising:
   providing a reaction solution comprising L-phenylalanine and an (R)-selective phenylalanine aminomutase, wherein said (R)-selective phenylalanine aminomutase synthesizes (R)-β-phenylalanine from L-phenylalanine;
   synthesizing (R)-β-phenylalanine beyond a saturation concentration or supersaturation concentration in said reaction solution, wherein said (R)-β-phenylalanine is precipitated out of the reaction solution as a solid; and
   collecting said solid (R)-β-phenylalanine from said reaction solution.

3. The method for producing (S)-β-phenylalanine according to claim 1, wherein the pH of the reaction solution is not less than 6 and not more than 10.

4. The method for producing (S)-β-phenylalanine according to claim 1, wherein the temperature of the reaction solution is not less than 4 degrees centigrade and is not more than a temperature in which said (S)-selective phenylalanine aminomutase is deactivated.

5. The method for producing (R)-β-phenylalanine according to claim 2, wherein the pH of the reaction solution is not less than 6 and not more than 10.

6. The method for producing (R)-β-phenylalanine according to claim 2, wherein the temperature of the reaction solution is not less than 4 degrees centigrade and is not more than a temperature in which said (R)-selective phenylalanine aminomutase is deactivated.

* * * * *